United States Patent
Madar et al.

(10) Patent No.: US 7,653,429 B2
(45) Date of Patent: Jan. 26, 2010

(54) TECHNIQUES FOR IDENTIFYING MOLECULAR STRUCTURES AND TREATING CELL TYPES LINING A BODY LUMEN USING FLUORESCENCE

(75) Inventors: Igal Madar, Baltimore, MD (US); John C. Murphy, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 2 days.

(21) Appl. No.: 12/252,436

(22) Filed: Oct. 16, 2008

(65) Prior Publication Data

US 2009/0035222 A1  Feb. 5, 2009

Related U.S. Application Data

(62) Division of application No. 10/633,446, filed on Aug. 1, 2003, now Pat. No. 7,515,953.

(60) Provisional application No. 60/400,325, filed on Aug. 1, 2002.

(51) Int. Cl.
*A61B 6/00* (2006.01)

(52) U.S. Cl. ............... 600/476; 600/172; 600/547; 600/153; 600/114; 348/68; 359/708

(58) Field of Classification Search ........... 600/431, 600/476; 348/68, 69; 378/65; 424/181.1; 128/899

See application file for complete search history.

(56) References Cited

U.S. PATENT DOCUMENTS 6,324,418 B1 * 11/2001 Crowley et al. ............. 600/476
2002/0168317 A1 * 11/2002 Daighighian et al. ........ 424/1.11

\* cited by examiner

*Primary Examiner*—Brian Casler
*Assistant Examiner*—Nasir Shahrestani
(74) *Attorney, Agent, or Firm*—Francis A. Cooch

(57) ABSTRACT

Techniques for detecting fluorescence emitted by molecular constituents in a wall of a body lumen include introducing an autonomous solid support into the body lumen. Cells in a lumen wall of the body lumen are illuminated by a light source mounted to the solid support with a wavelength that excites a particular fluorescent signal. A detector mounted to the solid support detects whether illuminated cells emit the particular fluorescent signal. If the particular fluorescent signal is detected from the illuminated cells, then intensity or position in the lumen wall of the detected fluorescent signal, or both, is determined. These techniques allow the information collected by the capsule to support diagnosis and therapy of GI cancer and other intestinal pathologies and syndromes. For example, these techniques allow diagnostic imaging using endogenous and exogenous fluoroprobes, treating diseased sites by targeted release of drug with or without photoactivation, and determining therapeutic efficacy.

3 Claims, 5 Drawing Sheets

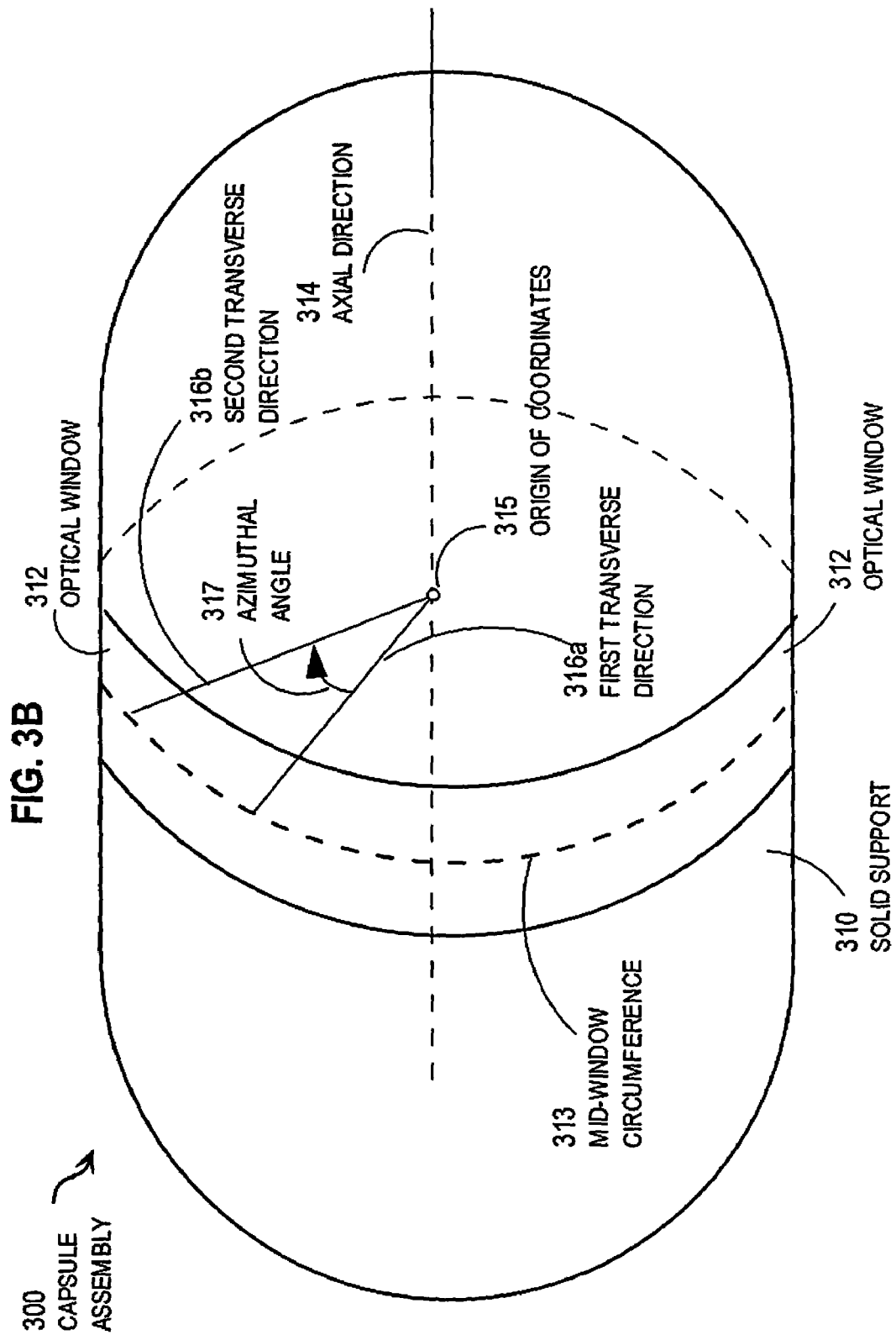

TECHNIQUES FOR IDENTIFYING MOLECULAR STRUCTURES AND TREATING CELL TYPES LINING A BODY LUMEN USING FLUORESCENCE

CROSS-REFERENCE TO RELATED APPLICATIONS

This application is a divisional of U.S. patent application Ser. No. 10/633,446, filed Aug. 1, 2003, U.S. Pat. No. 7,515,953, issued Apr. 7, 2009, which claims benefit of Provisional Appln. 60/400,325, filed Aug. 1, 2002, the entire contents of which are hereby incorporated by reference as if fully set forth herein, under 35 U.S.C. §119(e).

BACKGROUND OF THE INVENTION

1. Field of the Invention

The present invention relates to identifying molecular structures and cell types in walls of a body lumen in animals; and in particular to fluorescent imaging of cell types in walls of a body lumen for diagnosis or therapy, such as in vivo therapy based on selective destruction of labeled tumor cells. The invention has application to the diagnosis and treatment of intestinal cancer and colon cancer, among other pathologies and syndromes.

2. Description of the Related Art

Cancer of the gastrointestinal (GI) tract is easily treated if detected early. Consequently a great deal of activity has been expended in developing systems to inspect the GI tract for early signs of cancer. One of the first significant advances was the endoscope, which allows a doctor to inspect portions of the GI tract with a miniaturized light source at a probe end of a coherent bundle fiber optic cable. Reflected light beam images are returned through the fiber optic cable for detection by an external digital camera and display on an external monitor or for recording on an external video recorder or both.

While suitable for inspection of the esophagus, stomach and portions of the large intestine, the endoscope is neither capable of inspecting some portions of the large intestine (colon) nor capable of inspecting most of the small intestine.

In recent years, swallowable capsules containing miniaturized optical, digital camera and radio transmission systems have been developed along with complementary external monitoring systems for inspecting the small intestine. For example, one capsule and monitoring systems is marketed as M2A by Given Imaging Ltd. of Yokneam, Israel and another is marketed as NORIKA from RF SYSTEM Lab. of Nagano City, Japan. At the time of this writing, these systems are described on the World Wide Web at internet domains given-imaging.com and rfnorika.com, respectively. Elements of these systems are described in several patents, including U.S. Pat. No. 5,604,531 by G. V. Iddan and D. Sturlesi issued Feb. 18, 1997 (hereinafter Iddan I), the entire contents of which are hereby incorporated by reference as if fully set forth herein.

The capsule is swallowed by a patient and makes its way into the small intestine. As the capsule is pushed through the small intestine by peristalsis, it lights the wall of the intestine and captures images of the wall with the camera system and transmits those images to the monitoring unit outside the patient. The monitoring unit includes radio frequency (rf) receivers around the torso of the patient, a processor to interpret the signals received, a recorder to record the interpreted imagery, and a display to present the image to a technician or medical doctor. Because it can take the capsule about eight hours to traverse the intestinal tract, the data is often recorded first and the technician reviews a videotape replay that can be viewed in a shorter time, on the order of an hour.

While representing a great advance in imaging the morphology of the small intestine and the upper large intestine (upper colon), as well as other body openings (body lumen), there are still some deficiencies with the prior art capsule systems. Reflectance imaging such as that performed by both of the Givens and Norika systems monitor the morphology of the interior walls of the lumen i.e. shape in the form of growths or protrusions of the wall. In the earliest stages, some cancer cells and pre-cancerous cells do not form structures that can be distinguished by morphology from other structures found on the cell wall. In the more advanced stages, when tumors are apparent by their morphology, the prior art capsule systems can not distinguish between a tumor mass containing dying cells that are responding to treatment, and a tumor mass with viable cells that are resisting treatment or are continuing to grow. In other diseases of cells in the intestinal wall, abnormal cells, which otherwise appear morphologically the same as normal cells, are performing different functions and generating or ingesting different molecules, including different proteins. For example, such diseases include gastrointestinal motility, ischemia and protein-losing disorders. Therefore, existing capsule systems can not distinguish some significant disease-related types and functions of cells making up the structure of the walls.

Based on the foregoing, there is a clear need for techniques that determine cell types and functions in the walls of the small intestine or the upper large intestine or both.

In general, there is a need for techniques that determine cell types and functions in the walls of a body lumen, including the GI tract, a sinus passage, and a large blood vessel, among others.

SUMMARY OF THE INVENTION

According to various embodiments of the invention, the properties of fluorescent emissions to distinguish among molecular participants in cell processes are exploited to detect cell types or processes or both in the walls of a body lumen navigable by an autonomous capsule. The information collected by the capsule may be used to support diagnosis and therapy. In some embodiments the capsule also performs one or more therapeutic functions, such as activating photo-active toxins. Aspects of the present invention are directed to the capsule and a monitoring unit and system, and to methods that use the capsule for measuring fluorescence from cells lining a body lumen, and for diagnosing and treating diseases involving those cells.

According to one aspect of the invention, a method for determining cell types or functions in the walls of a body lumen includes introducing an autonomous solid support into the body lumen. Cells in a wall of the body lumen are illuminated by a light source mounted to the solid support with a wavelength that excites a particular fluorescent signal. A detector mounted to the solid support detects whether illuminated cells emit the particular fluorescent signal. If the particular fluorescent signal is detected from the illuminated cells, then intensity or position in the lumen wall of the detected fluorescent signal, or both, is determined.

In various embodiments the signal is from endogenous or exogenous fluorophores or both.

According to an embodiment of this aspect, an image is formed that indicates positions in the lumen wall where the particular fluorescent signal is detected.

According to another embodiment of this aspect, an exogenous fluorescent-labeled probe that binds to or is internalized by certain cells in the lumen wall is introduced to cells in the lumen wall including the illuminated cells. The exogenous probe can be inserted into the lumen wall through the blood or alimentary system via selective uptake in tumor tissue or by direct release within the lumen from the capsule with subsequent uptake by cells within the lumen wall, or by any other means known in the art. The exogenous probe emits the particular fluorescent signal in any case.

According to another embodiment, the exogenous fluorescent-labeled probe is released from a reservoir on the solid support. In some such embodiments, the exogenous fluorescent-labeled probe is taken up locally by cells in the lumen wall.

According to another embodiment, to enhance local uptake of the exogenous probe, ultrasonic waves are emitted from a sound source on the solid support.

According to another embodiment, to enhance uptake of the exogenous probe, an electric field is generated from an electrode on the solid support.

According to another aspect of the invention, a method for detecting fluorescence emitted by intestinal cells in vivo includes introducing an autonomous solid support into the lumen of the intestine. Cells in the intestine wall are illuminated from a light source mounted to the solid support with a wavelength that excites a particular fluorescent signal. A detector mounted to the solid support detects whether illuminated cells emit the particular fluorescent signal. If the particular fluorescent signal is detected from the illuminated cells, then intensity or position in the intestine of the detected fluorescent signal, or both, is determined.

According to another aspect of the invention, a method for killing abnormal cells in the intestinal tract of an animal includes administering to the animal an exogenous fluorescent-labeled probe that is selectively internalized by or binds to abnormal intestinal cells. An autonomous solid support is introduced into the lumen of the intestine. Cells in the intestinal wall are illuminated from a light source mounted to the solid support with a wavelength that excites a particular fluorescent signal emitted by the fluorescent label on the exogenous probe. A detector mounted to the solid support detects whether illuminated cells emit the particular fluorescent signal. If the particular fluorescent signal is detected, then drug is released that kills the abnormal intestinal cells. In some embodiments, a therapeutic optical signal is emitted from the solid support that excites the fluorophore or a photo-active toxin in the drug and kills the abnormal intestinal cells.

According to another aspect of the invention, a method for killing abnormal cells in the intestinal tract of an animal includes administering to the animal an amount of one or more exogenous probes that are selectively internalized by or bind to abnormal intestinal cells. At least one probe is bound to a fluorescent label and at least one probe is bound to a light-activated toxin. In many cases the light activated toxin and the fluorescent label are one and the same. An autonomous solid support is introduced into the lumen of the intestine. Cells in the intestinal wall are illuminated from a light source mounted to the solid support with a wavelength that excites a particular fluorescent signal emitted by the fluorescent label on the exogenous probe. A detector mounted to the solid support detects whether illuminated cells emit the particular fluorescent signal. If the particular fluorescent signal is detected, then the cells are illuminated with light to activate the light-activated toxin to kill the abnormal cells.

According to another aspect of the invention, a method for determining the efficacy of treatment of cancer in the upper or lower intestinal tract in an animal, or both, includes administering to the animal having cancer of the upper or lower intestinal tract an amount of an exogenous fluorescent-labeled probe that is selectively internalized or bound by the cancer cells. The cells in the intestinal wall are illuminated from a light source mounted to a first autonomous solid support introduced into the lumen of the intestine with a wavelength that excites a particular fluorescent signal emitted by the fluorescent label on the exogenous probe in the cancer cells. A detector mounted to the first solid support detects the fluorescent signal emitted by the exogenous probe in cancer cells illuminated to determine a first amount of fluorescent emission. After determining the first amount of fluorescent emission, a treatment is administered to the animal to eliminate the cancer cells. After administering the treatment, an amount of the exogenous fluorescent-labeled probe is administered to the animal. Cells in the intestinal wall are illuminated from a light source mounted to a second autonomous solid support introduced into the lumen of the intestine with the wavelength that excites the particular fluorescent signal. A detector mounted to the second solid support detects the fluorescent signal emitted by the exogenous probe in cancer cells to determine a second amount of fluorescent emission. An efficacy of the treatment is determined based on a difference between the first and second amounts of fluorescent emission. In some embodiments, the first and second solid supports are the same.

According to another aspect of the invention, a capsule for detecting fluorescence emitted by cells in a wall of a body lumen in a patient includes a solid support that fits inside a body lumen. A light source is mounted to the solid support for generating light with a wavelength that excites a particular fluorescent signal in certain molecules. A first optical element is mounted to the solid support for illuminating a section of a lumen wall of the body lumen with light from the light source. A detector is mounted to the solid support for generating measurements based on the particular fluorescent signal. A second optical element is mounted to the solid support for directing onto the detector the particular fluorescent signal emitted from the section illuminated. A data transfer system is included for transferring data based on the measurements to a monitoring unit outside the patient.

According to an embodiment of this aspect, the second optical element includes a filter to block out light at wavelengths not part of the particular fluorescent signal.

According to an embodiment of this aspect, the capsule also includes a reservoir and a release mechanism. The reservoir stores at least one of an exogenous fluorescent-labeled probe and a drug for killing abnormal cells. The release mechanism releases contents of the reservoir upon command. According to another embodiment, the capsule also includes an electrode for generating an electric field to enhance uptake of the contents of the reservoir by cells in the lumen wall after release of the contents. According to another embodiment, the capsule also includes an acoustic transducer for generating acoustic waves to enhance uptake of the contents of the reservoir by cells in the lumen wall after release of the contents.

According to another aspect of the invention, a monitoring unit for presenting fluorescence emitted by cells in a wall of a body lumen in an animal, includes a receiver for receiving data from a capsule that fits inside the body lumen. The capsule includes a solid support, a light source, a detector, and a data transfer system. The light source is mounted to the solid support for generating light with a wavelength that excites a particular fluorescent signal in certain molecules. The detector is mounted to the solid support for generating measurements based on the particular fluorescent signal emitted by an illuminated section of the lumen wall. The data transfer system transfers data based on the measurements to the receiver. The monitoring unit also includes a processor to generate an image based on the data, and a display for presenting the image to a user.

According to another aspect of the invention, a system for detecting fluorescence emitted by cells in a wall of a body lumen in a patient, includes a capsule and a monitoring unit. The capsule includes a solid support that fits inside a body lumen and a light source, a detector, and a data transfer system. The light source is mounted to the solid support for generating light with a wavelength that excites a particular fluorescent signal in certain molecules. The detector is mounted to the solid support for generating measurements based on the particular fluorescent signal emitted from an illuminated section of the body lumen. The data transfer system is mounted to the solid support for transferring data based on the measurements. The monitoring unit includes a receiver for receiving the data from the capsule, a processor to generate an image based on the data, and a display for presenting the image to a user.

BRIEF DESCRIPTION OF THE DRAWINGS

The present invention is illustrated by way of example, and not by way of limitation, in the figures of the accompanying drawings and in which like reference numerals refer to similar elements and in which:

FIG. 3B is a perspective drawing to indicate three dimensional directions and coordinates relative to the capsule, according to an embodiment.

DETAILED DESCRIPTION

Figure 1:
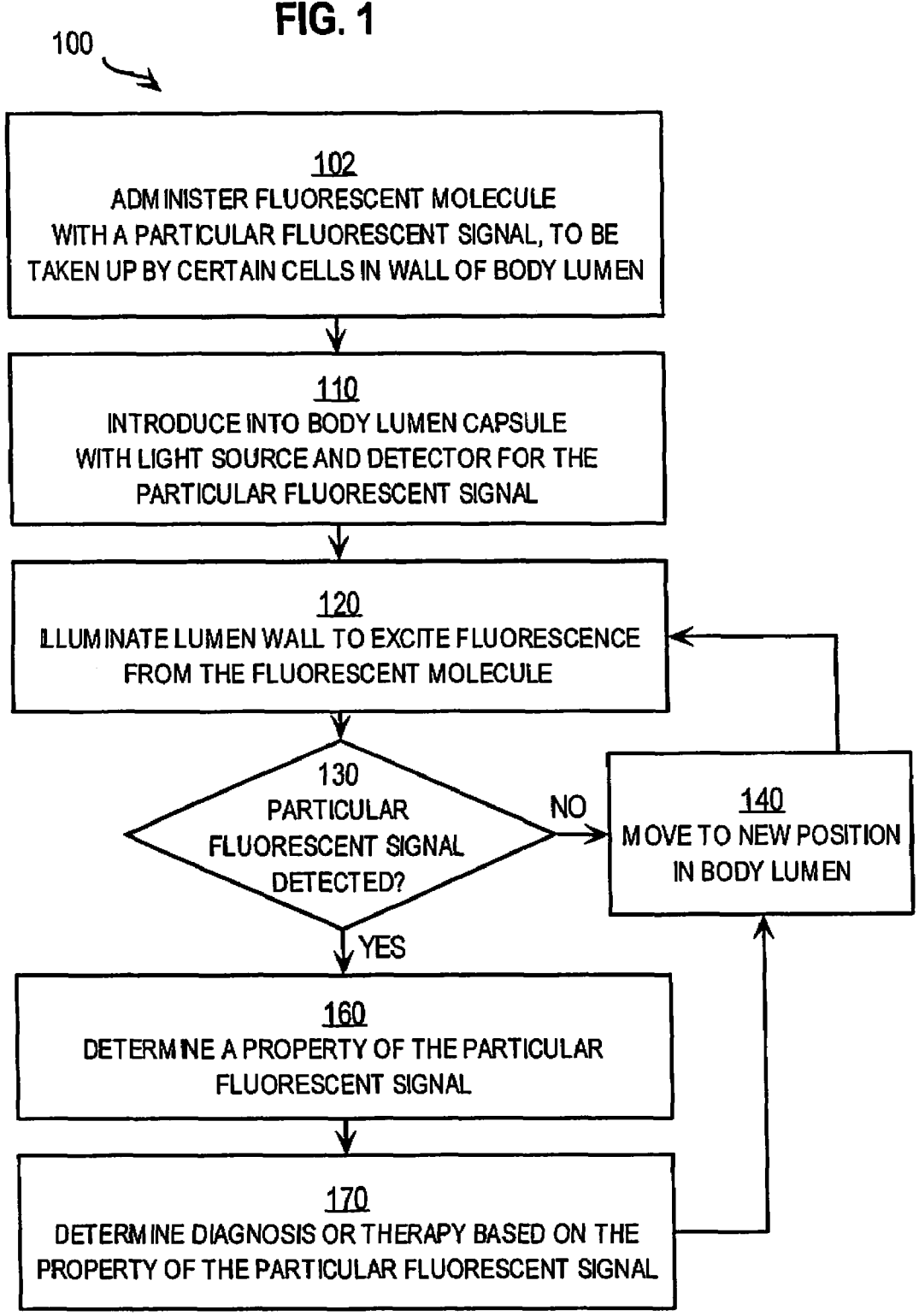
FIG. 1 is a flow diagram that illustrates at a high level a method for identifying cell types and functions in a wall of a body lumen, according to an embodiment.

A method and apparatus are described for quantitative identification of specific molecular structures and tissue constituents as well as cell type and functions in the walls of a body lumen. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Embodiments of the invention are described primarily in the context of diagnosis and therapy for dysfunction of the human intestinal tract, but the invention is not limited to this context. For example, in other embodiments the techniques may be applied to non-human animals. Furthermore, in other embodiments, the techniques may be applied to body lumen other than the intestinal tract, such as the stomach, esophagus, nasal passages, trachea and blood vessels. As used herein, body lumen includes any lumen into which the capsule can be introduced, including the nose, esophagus, stomach, and intestine. As used herein, the intestine includes the small and large intestine, colon, and rectum.

Embodiments of the invention are described in the following sections.

1. Functional Overview

2. Fluorescent Indicators of Biological Functions
   2.1 Natural fluorescent markers of biological functions—endogenous probes
   2.2 Fluorescent-labeled markers of biological functions—exogenous probes
   2.3 Light-activated toxins bound to markers of biological functions 3. Method for Performing Functional Imaging 4. System for Performing Functional Imaging
   4.1 Structural overview
   4.2 Autonomous capsule assembly
   4.3 External assembly 5. Processor Hardware Overview 1. Functional Overview According to various embodiments of the invention, fluorescent signals are used to identify molecular structures (e.g., proteins, enzymes), tissue constituents (e.g., collagen), blood components (e.g., hemoglobin) and specific populations of cells that line a body lumen, such as the intestine, based on their specific fluorescence signature. Pathologies are associated with microscopic morphological changes that can be detected by fluorescence imaging but not by the naked eye. The specific populations of cells can be normal cells or abnormal cells like cancer. The fluorescent signal can be emitted by fluorescent-labeled probes that are selectively bound to or internalized by target molecules in specific populations of cells hereafter referred to as "exogenous fluorescence", or by naturally occurring molecules present in the cells, which have intrinsic fluorescence hereafter referred to as "endogenous fluorescence." In either case the molecule which fluoresces that is the object of the measurement by the capsule is called the target molecule. The detection of fluorescent signals emitted by cells lining a body lumen is accomplished by introducing to the lumen an autonomous capsule capable of exciting fluorescence in the target molecule, detecting the fluorescent signal emitted by the target molecule, if any, and transmitting data on the intensity or position of the fluorescent signals or both.

The limited depth of penetration of excitation light in tissue from an external light source limits the depth of excitation of fluorescent molecules in a patient's body to distances of about 2000-3000 g/m (microns, 1 $\mu m=10^{-6}$ m) in the near infrared portion of the electromagnetic spectrum. The near infrared includes wavelengths from about 650 to 1000 nm (nanometers, 1 $nm=10^{-9}$ m). In the visible portion of the spectrum, the depth of penetration is smaller and may reach only about 200 to 300 $\mu m$. Similarly, the fluorescent signal must have sufficient energy to exit the body in order to be detected. Fluorescent emissions from cells in regions of the intestine outside the range of fiber optic endoscopes are undetectable with prior techniques that attempt to measure fluorescence from the exterior surface of a patient's body.

By introducing a capsule of the present invention into a body lumen, the capsule is in direct contact with or close proximity to the wall of the lumen to excite fluorescent molecules and detect fluorescent signals emitted from cells in the lumen wall. These signals are not measurable at detectors outside the body lumen using current technologies.

Prior capsules, which also travel through the small intestine and other body lumen, only detect light from a light source that is reflected from the lumen. A broadband white light source or one or more narrowband light sources, or some combination, are used to let an operator look for macroscopic morphological abnormalities like larger tumors, polyps, adenoma and inflamed tissue and in some cases color variations in the reflected light that are apparent in reflected color images.

According to embodiments of the invention, the capsule has a light source for emitting light (hereinafter "excitation light") that excites the fluorescence of the target molecule and a detector for measuring the specific fluorescent response of the target molecule. The capsule also has a data transfer system for transferring data representing the measurements to an external monitoring unit to view the data, either after removal of the capsule from the body lumen or while the capsule is still inside. An illustrated embodiment of the capsule is described in a later section. Information collected by the capsule may be used to support diagnosis and therapy of diseases affecting cells lining the lumen. In some embodiments, the capsule also has one or more reservoirs for dispensing material, such as the fluorescent-labeled probes. In some embodiments the capsule also performs one or more therapeutic functions, such as dispensing medication locally, or dispensing fluorescent-labeled probes conjugated to toxins capable of killing the cells that selectively take up the probes, among others, or combinations of these therapies. In some embodiments, when the capsule releases material from a reservoir, the capsule enhances uptake of the released material into cells of the lumen wall by emitting a pulsed electric field to incite electroporation, or by emitting ultrasonic waves to incite sonoporation, or both.

FIG. 1 is a flow diagram that illustrates a method for identifying cell types and functions of cells in a wall of a body lumen, according to an embodiment. Although steps are depicted in FIG. 1 in a particular order for purposes of illustration, in other embodiments the steps may be performed in a different order or overlapping in time. For example, in some embodiments step 102 is performed after step 110 and in other embodiments, step 102 is omitted, as is the case when endogenous fluorescence in cells lining a body lumen is being assessed, as described in more detail in a later section.

In step 102, a fluorescent-labeled probe that will be taken up selectively by a population of cells in a lumen wall, such as malignant cells, is administered to a patient. Any method to administer the fluorescent-labeled probe molecule may be used, such as injection into the blood stream, injection into the nearby tissue, oral ingestion, and local release from a point inside the respective body lumen, among others.

In those embodiments where a fluorescent-labeled probe is released locally into the body lumen from a reservoir on the capsule, step 102 is performed after step 110, described next. In some embodiments, when the fluorescent-labeled probe is released from a reservoir on the capsule, the capsule emits a pulsed electric field or ultrasonic waves to enhance uptake of the probe by electroporation or sonoporation, respectively, or both.

In some embodiments, differences in the amount of endogenous fluorescence is used to identify normal and abnormal cells. In some such embodiments, step 102 is omitted.

In step 110, the capsule is introduced into the body lumen, such as into the small intestine. Any method may be used to introduce the capsule into the lumen. For example, to introduce a capsule into the small intestine, the capsule can be swallowed by the patient, placed into the opening of the small intestine with a tool such as an endoscope, or surgically implanted. The first example method is least invasive for the patient.

In step 120, a section of the lumen wall is illuminated by the light source on the capsule with a specific wavelength to excite the fluorescence of the target molecule—either the exogenous fluorescent-labeled probe (introduced in step 102) or a naturally occurring molecule known to emit endogenous fluorescence. Any method known for illuminating the intestinal wall from a light source on the capsule may be used. A particular embodiment is described in a later section. In some embodiments, the illumination includes other wavelengths in addition to the specific wavelength to excite fluorescence of the target molecule.

In step 130, it is determined whether a fluorescent signal emitted from the target molecule is detected at the detector. If detected, control passes to step 160; if not, control passes to step 140. Any method for detecting fluorescence on the capsule may be used. Step 130 includes obtaining measurements from the detector. For example, step 130 includes measuring the intensity of light striking the detector at one or more specific wavelengths of the fluorescent signal.

In step 140 the capsule moves to another position along the length of the intestine (either under its own power or by allowing peristalsis or some other external force to move the capsule). In some embodiments step 140 includes reporting on the position of the capsule by sending a radio frequency (rf) signal to an external monitoring unit. In some embodiments the negative result from the detector is recorded or reported on the rf signal to the monitoring unit for forming an image.

In step 160, a property of the fluorescent signal is determined based on the measurements made by the detector. For example, in some embodiments, a ratio of the intensity of two wavelengths of the fluorescent signal is determined. As a further example, in various embodiments, the intensity of the fluorescent signal or a ratio is determined for the entire illuminated section or for various portions of the illuminated section. In some embodiments, each spatial portion of the illuminated section for which intensity is separately determined becomes another pixel in an image that is generated. In some embodiments, step 160 includes determining the positions of multiple portions of the illuminated section and therefore multiple pixels from each illuminated section. In some embodiments an image is constructed from the pixels generated by several occurrences of step 160 as the capsule moves through the intestine.

In step 170, a diagnosis or therapy is determined based on the property of the fluorescent signal of the target molecule that results from step 160. For example, it is determined that the illuminated section of the intestine is cancer free, if there is no fluorescent signal from a fluorescent-labeled probe that specifically binds to or is internalized by cancer cells, or from an endogenously fluorescent molecule associated with malignant cells. In such embodiments, the detection of a fluorescent signal determines the presence of malignant cells. Analysis of the intensity and location of the fluorescence is used to create images of the location of the cancer cells. In some embodiments, a biopsy is taken at a potentially cancerous location indicated by the fluorescent signal. In some embodiments, some or all of step 170 is performed based on data sent to the external monitoring unit in a previous step 140. In some embodiments, part or all of step 170 is performed on an information processor on the capsule.

In some embodiments, step 170 further includes performing therapy functions, such as releasing a drug locally from a reservoir on the capsule to kill cancer cells in the section of the intestine recently illuminated, or to illuminate the section again to activate a photo-active toxin, such as described below, or both. In some embodiments, which release the drug, electroporation or sonoporation, or both, are employed to enhance uptake of the drug by the nearby cells.

After step 170, control passes to step 140 to report measured data and move further along the intestine, as described above.

Steps of method 100 may be performed by the capsule or a system that includes the capsule. For example, in some embodiments, image formation and analysis is performed by components on the external monitoring unit. A system that includes the capsule is described in more detail in a later section.

2. Fluorescent Indicators of Biological Functions

The components on the capsule and the use of the data gathered by the capsule depend on the target molecule or molecules that are to be excited by the light source and detected by the detector. In this section, examples of endogenous and exogenous fluorescent molecules and their relationships to cell functions or specific cell types or both are described.

The use of fluorescent-labeled exogenous probes to follow the synthesis, movement and uptake of biological molecules is well known in the art. For example, fluorescent labels are commonly used with in vitro studies to label both monoclonal and polyclonal antibodies, antigens, proteins, enzymes and peptides. The labeled molecule is illuminated at wavelengths that cause fluorescent emission that is detected using a fluorescent microscope or a sensor that detects the particular wavelength of the fluorescent signal emitted from the label.

The use of fluorescent labels to diagnose and treat diseases has been severely limited by the low energy wavelengths of fluorescent labels such as Rhodamine 123. There is no existing technology capable of detecting fluorescent signals emitted by fluorophores such as Rhodamine 123 from cells more than about several hundred microns deep inside the body because the energy of the emitted fluorescent signal is not strong enough to be detected with known technology.

2.1 Natural Fluorescent Markers of Biological Functions—Endogenous Probes

Many molecules (including proteins, peptides, DNA, and RNA, among others) will fluoresce if excited by an appropriate wavelength of excitation light. These molecules therefore are sources of endogenous fluorescence that can be used as markers to identify particular populations of cells and to monitor metabolic processes. Fluorescent emissions from specific antigens, proteins or other molecules that are selectively produced, internalized or bound by abnormal diseased cells (hereafter "disease markers") can be used to locate the respective diseased cells and monitor the response of those cells to drug therapy using the methods described below. In order for such endogenous molecules to be useful as markers, their emission wavelengths must be unique compared to other molecules in the target cells. Specific populations of normal cells can similarly be identified if they produce or accumulate molecules with unique fluorescence patterns compared to abnormal cells.

Endogenous fluorescence can distinguish between normal, pre-cancerous (adenomas) and cancerous tissue. The fluorescence intensity of normal tissue is significantly greater than pre-cancerous tissue, which is greater than cancerous tissue. Visible tissue autofluorescence is typically dominated by only a few fluorophores, including collagen, elastin, nicotinamide adenine dinucleotide (NADH), nicotinamide adenine dinucleotide phosphate (NADPH), flavins, porphyrin and triptophan. Collagen is regarded as the major contributor of autofluorescence in the colon (Zonios, et al., "Morphological model of human colon tissue fluorescence," IEEE Trans. Biomed. Eng., vol. 43, no. 2, pp 113-122, 1966). Blood hemoglobin is also a major source of absorption of fluorescent emissions from collagen (Brown, 1980 "An introduction to spectroscopy to biochemists" Academic Press, London, England). Epithelial tumors such as colonic adenomas are often characterized by an epithelial thickening that shield submucosa connective tissue constituents (e.g., collagen) thereby causing a decrease in the amount of light emitted by the endogenous fluorophores in the connective tissue. This phenomenon has been referred to as a "red shift". For example, areas suspected of having a colonic adenoma emit light in the red-brown range, while healthy tissue emits light in the yellow-green range of the spectrum (Izuishi et al., "The histological basis of detection of adenoma and cancer in the colon by autofluorescence endoscopic imaging," Endoscopy, vol 31, no. 7, pp 511-516, 1999). Other factors that may attenuate emitted fluorescence intensity include increased absorption by hemoglobin as a result of an increased blood supply in the malignant area, and increased amount of a reduced form of NADH, and reduced NADPH or flavins or both. Excitation of these endogenous fluorophores with the respective excitation wavelength of fluorescent light will distinguish normal from abnormal cells. Monitoring changes in fluorescence as an indicator for pre-cancerous and cancerous tissue has thus far been limited by an optic fiber field of view having a diameter of about 600 micrometers, and a depth of fluorescence detection of about 200 to about 450 μm. One embodiment of the method and system of the present invention can be used to locate malignant adenomas or dysplastic cells lining a body lumen where optic fibers cannot be used. In one embodiment red shift in emission of fluorescence from endogenous sources is measured and used to detect pre-cancerous and cancerous sites.

Dopamine is a neurotransmitter that fluoresces at a wavelength of about 550 nm; it therefore is used in some embodiments as an endogenous fluorescent marker to identify populations of neurons located in or innervating a body lumen that synthesize and accumulate significant amounts of this compound.

2.2 Fluorescent-Labeled Markers of Biological Functions—Exogenous Probes

In many embodiments of the present invention, molecules that bind specifically to or are internalized by targeted cells are artificially bound to well-characterized fluorescent labels to form fluorescent-labeled probes before being administered to a patient. These exogenous fluorescent-labeled probes can target normal or abnormal cells. In some embodiments the exogenous fluorescent-labeled probes are monoclonal or polyclonal antibodies directed against specific cell surface antigens on the targeted cells. Any molecule that can be bound to a fluorescent label is a potential probe, including synthetic, non-naturally occurring or even inorganic molecules. Proteins, protein precursors, peptides, antisense DNA or RNA, lipids or other biological molecules can be labeled with fluorescent molecules for use as probes. Even though the patient may synthesize some of these probes naturally, the fact that they are artificially labeled and administered to the patient places them in the category of exogenous probes. Exogenous fluorescent-labeled probes are administered to a patient by routes known in the art, including intravenous and oral administration, among others. As will be discussed in section 3 below, exogenous fluorescent-labeled probes can also be dispensed locally inside a body lumen using the methods of the present invention. To accomplish this, the probe is released from a reservoir on a capsule that has been administered to a patient.

One fluorescent-labeled exogenous probe for use in some embodiments is fluorescent-labeled 2-deoxyglucose that is taken up by cells as is normal glucose. However, unlike glucose, 2-deoxyglucose is not broken down inside the cell. It therefore accumulates in the cell and serves as a probe molecule in some embodiments. Malignant cells take up and accumulate 2-deoxyglucose at a significantly faster rate than normal cells, making 2-deoxyglucose a useful marker for transformed cells. While computed tomography (CT) scans have an unacceptably high rate of approximately 33% failures (false positives and false negatives), 2-deoxyglucose uptake as a marker of malignant cells generates only about 10% failures.

Another example of a fluorescent-labeled exogenous probe that can be used to identify malignant cells is fluorescein labeled phosphonium cations (PhCs), which are taken up selectively by malignant cells as a function of mitochondrial dysfunction. Phosphonium ions labeled with radioisotopes are being evaluated for use in humans as a radioprobe for positron emission tomography (PET). F-18 labeled phosphonium cations have been developed with a molecular size and structure, lipophilicity and positive charges optimized to obtain metabolic stability, high accumulation in cells, high sensitivity to mitochondrial membrane potential and minimal intervention of efflux mechanisms, such as multi-drug resistance. Studies in isolated mitochondria and cardiovascular toxicity in dogs show that PhCs at 1,000 fold the dose used in humans are harmless. PET studies show that PhCs enable the detection of solid tumors at a high contrast, indicating significant levels of uptake, and are able to differentiate malignancy from inflammation, thus eliminating surgeries or drug therapy of false positive cases. Moreover, PhCs differentiate pre-cancerous lesions at early stages of the molecular progression toward invasive carcinoma, including early stages of hyperplasia, dysplasia and carcinoma in-situ. The properties of PhCs are described in more detail in PCT published application PCT/US03/03740, "Non-Invasive Diagnostic Imaging Technology for Mitochondria Dysfunction Using Radiolabeled Lipophilic Salts" by I. Madar, H. T. Ravert, R. F. Dannals, U. Scheffel and J. J. Frost, the entire contents of which are hereby incorporated by reference as if fully set forth herein.

Fluorescent-labeled exogenous probes can be useful for a sensitive and rapid assessment of tumor response to therapy. Conventional radiographic methods (X-ray, CT) for assessment of efficacy of chemotherapy agents rely on alterations in tumor size. This approach is slow and usually involves multiple chemotherapy cycles over several months of treatment. The present methods enable the use of fluorescent-labeled exogenous probes to image target molecules specific to tumor cells, thus making it possible to detect and measure the response of the tumor to treatment within a few days with much greater sensitivity than can be obtained with other methods. This is accomplishing by using fluorescent probes to target specific molecular events activated by the chemotherapy agent. Most major anticancer drugs (e.g., taxens, cis-platinum, doxorubicin) induce cell death via a process termed apoptosis. The apoptotic cell death involves the externalization of the membrane protein phosphatidyl serine. In one embodiment, externalized phosphatidyl serin is detected using fluorescent Annexin V. Alternatively, apoptosis can be detected using fluorescent probes that accumulate in mitochondria as a function of electrical gradient across the membrane—such probes are termed voltage indicators. A major pathway of apoptosis involves the collapse of the mitochondrial electrical gradient, which results in reduced accumulation of fluorescent voltage indicators such as rhodamine-123, and 5,5',6,6'-tetrachloro-1,1',3,3'-tetraethylbenzimidazolcarbocyanine iodide (JC-1), and tetramethylrhodamine ethyl ester (TMRE) and phosphonium cations (Madar et al., "Physiochemical Characteristics and Uptake Kinetics of Voltage Indicator [F-18]Phosphonium Cations," Journal of Nuclear Medicine [JNM] vol. 44, p 50P, 2003; Madar et al., "Quantitative Imaging of Cardiomyopathy in Heart Failure Using the Voltage Indicator [F18]p-Florobenzyl Triphenylphosphonium ([F-18]p-FBnTP) and PET," JNM vol. 44, p 87P, 2003; Madar et al., "In Vitro and In Vivo Correlation of Taxotere-induced Apoptosis in Malignant Cells and Accumulation of the Voltage Indicator [F18]p-Florobenzyl Triphenylphosphonium ([F-18]p-FBnTP)," JNM vol. 44, p 179P, 2003; Madar et al., "Detection of Androgen Depletion-Induced Apoptosis in Prostate Using the Voltage Indicator [F18]p-Florobenzyl Triphenylphosphonium ([F-18]p-FBnTP), In Vivo," JNM vol. 44, p 180PP, 2003; Madar et al., "Differential Distinction Between Tumor and Inflammation Using the Voltage Indicator [F-18]p-Fluorobenzylriphenyl Phosphonium (F-18]p-FBnTP): Comparison with [F-18]FDG," JNM vol. 44, p 368P, 2003).

Ideally the fluorophores attached to the exogenous probes are non-toxic. However, only a limited number of fluorophores have been approved for use in humans, including tetracyclines, methylene blue and fluorescein. In some cases, the fluorophore that gives the best signal may not yet be approved for use in the host or may have higher levels of toxicity than have been approved for systemic administration. Probes labeled with these fluorophores are still useful for animal studies. It should be pointed out that, in certain embodiments, the toxicity to the patient is reduced by dispensing the probes locally from a reservoir on the capsule, thereby avoiding systemic administration of high doses of an unapproved or toxic fluorophore.

Fluorescent labels known in the art include 5-(and 6-)-carboxyfluorescein diacetate, succinimidyl ester (CFDA/SE), Aequorea green fluorescent protein (GFP), a two-photon fluorophore (C625), red fluorescent protein (dsRed) from discosoma (coral), cyanine dye, 3,3-diethylthiadicarbocyanine, carboxyfluorescein diacetate succinimidyl ester (CFSE), intrinsically fluorescent proteins Coral red (dsRed) and yellow (Citrine), fluorocein, rhodamine 123, Sulforhodamine (red), Dinitrophenyl (yellow), Dansyl (yellow) and safranin O. Any fluorescent molecule known in the art can be used with the present methods to label exogenous probes.

Local administration from the capsule is also desirable where the probe is expensive to make, as may be the case with certain monoclonal antibodies, antisense DNA, receptor agonists and antagonists, among others.

2.3 Light-Activated Toxins Bound to Markers of Biological Functions

Fluorescent photo-sensitizers that are presently used in photo-dynamic therapy demonstrate some degree of tumor selectivity and become toxic upon illumination with certain wavelengths of light. Fluorescent photo-sensitizers include porphyrins such as hematoporphyrin, 5-aminoluvulinic acid (ALA), photofrin, polyhematoporphyrin, and mesotetrahydroxyphenylchlorin. Once the photo-sensitizers have been internalized by the malignant cells, illumination with the appropriate excitation wavelength initiates toxicity that kills the cancer. In some embodiments the fluorescent photo-sensitizers are used as the photo-active toxins described above.

Non-cell-selective photo-sensitizers may also be used if locally dispensed and locally illuminated from one or more capsules.

3. Method for Performing Functional Imaging

Methods of the present invention are based on the use of a capsule that emits excitation light of defined wavelengths and detects fluorescent emissions. In many embodiments, the capsule is small enough to be swallowed, thereby permitting its noninvasive introduction into the intestine.

The methods in several embodiments are dynamic and multifaceted compared to prior techniques. The new methods permit the functional analysis of normal and abnormal cells (including assessing metabolic pathways and physiologic responses) in ways that are outlined below, based on the expression of endogenously fluorescent molecules or the interaction with exogenous fluorescent-labeled probes in the lumen wall. New methods for treating diseases and assessing the efficacy of drug therapy on diseases of cells lining the lumen are also provided.

Various embodiments of the methods are used in the following scenarios:

1. To detect abnormal cells using endogenous fluorescence. In step 170 the amount and distribution of endogenous fluorescence are assayed. In various embodiments the specific endogenous fluorescent molecules include
   a. endogenous fluorescent molecules only present in abnormal cells;
   b. endogenous fluorescent molecules not present in certain types of abnormal cells, or
   c. endogenous fluorescent molecules that emit either more or less fluorescence or that change fluorescent excitation wavelengths in abnormal cells compared to normal cells.
2. To detect abnormal cells using exogenous fluorescence. In step 102 the specific exogenous fluorescence is administered. In step 170 the amount and distribution of specific exogenous fluorescence are assayed. In various embodiments, exogenous fluorescent probes include
   a. exogenous fluorescent probes that only bind to or are internalized by abnormal cells,
   b. exogenous fluorescent probes that are not bound to or are not internalized by abnormal cells, or
   c. exogenous fluorescent probes that bind differentially to abnormal cells compared to normal cells.
3. To detect specific types of cells lining a body lumen that synthesize or store significant amounts of a particular endogenous molecule characteristic of that cell type. For example, endogenous fluorescence of dopamine can be used to identify dopaminergic neurons present in or innervating the lining of a lumen. In step 170 the amount and distribution of endogenous fluorescence of dopamine is assayed.
4. To detect specific types of cells lining a body lumen, which synthesize or store significant amounts of a particular exogenous molecule characteristic of that cell type. For example, cells that make a particular characteristic protein can be identified by introducing in step 102
   a. fluorescent-labeled antibodies directed against the protein,
   b. fluorescent-labeled precursors that are incorporated into the protein during biosynthesis, or
   c. fluorescent-labeled antisense RNA to messenger RNA for the protein.
   In step 170 the amount and distribution of the exogenous fluorescent-labeled probe is assayed
5. To use the same fluorophore that identifies abnormal cells as a therapeutic agent. For example, in step 102 fluorescent photo-sensitizers such as porphyrins are introduced. In step 120 they are illuminated. In step 170 the location of malignant cells are identified. In some embodiments the cells are illuminated again at greater intensity or different wavelength. When illuminated with the appropriate excitation light, the fluorescent photo-sensitizers become toxic and destroy the abnormal cells that took them up. In some embodiments the illumination to activate toxicity is performed during step 120, and in some embodiments during step 170.
6. To target drug delivery to abnormal or cancer cells. A capsule having a reservoir of drug is introduced in step 110 and eventually moves during step 140 to a position of a tumor. The position of the tumor is identified using one of the methods described above or is identified using prior or other technology, such as computed tomography (CT) scans, positron emission tomography (PET), nuclear magnetic resonance (NMR) imaging and X-rays, or some combination. During step 170 the drug is released locally. This enables relatively higher doses of drugs to reach the target cells than would be achieved with systemic administration, while minimizing side effects, and minimizing adverse drug interactions such as may occur when the patient is taking other medication. In some embodiments, step 170 includes electroporation or sonoporation to enhance uptake of the drug. In some embodiments the drug includes a photo-sensitizer that is not labeled with fluorescence but is activated by illumination from the light source on the capsule during step 170.
7. To target biopsy on abnormal or cancer cells. A capsule having a tissue sample mechanism is introduced in step 110 and eventually moves during step 140 to a position of a tumor. The position of the tumor is identified using one of the methods described above. In some embodiments the capsule is oriented during step 140 using movement control to position the tissue sample mechanism adjacent to the abnormal cells. During step 170 the tissue is sampled.
8. To assess efficacy of treatment. A measurement of the extent of abnormal cells before therapy is made during step 170 using one of the methods described above from a first capsule. Treatment is administered. In various embodiments, treatment is administered externally or during step 170 from the first capsule or from a second capsule using one of the therapies described above. A measurement of the extent of abnormal cells after therapy is made during step 170 using one of the methods described above from the first capsule or the second capsule or a third capsule. The difference in extent of abnormal cells is used as a measure of efficacy of the treatment.

Embodiments of some of these scenarios are described in more detail in the following paragraphs.

In some cases, diseased cells such as a tumor are identified using prior technology such as CT scans, PET, NMR and X-rays. However, these methods have significant levels of false positives. Therefore it is desirable to confirm the diagnosis before undertaking surgery or drug therapy that might be unnecessary. In one embodiment, a patient suspected of having intestinal cancer, based on one of the prior technologies, is treated. First, a fluorescent probe that is selectively taken up by malignant cells is administered in step 102. The patient is then given a capsule to swallow in step 110. Malignant cells are located in the intestine by emitting light having the appropriate excitation wavelength from a light source on the capsule in step 120. If fluorescence is detected in step 130, the presence of malignant cells is confirmed in steps 160 and 170. The capsule collects data on the intensity and location of fluorescent emitting cells in step 160, which can be used to generate an image of the fluorescing malignant cells in step 170, either on the capsule or in an external component of the system. In one embodiment, the fluorescent probe administered in step 102 is fluorescent-labeled phosphonium cations.

In an alternate embodiment, the fluorescent-labeled probe is released from a reservoir on the capsule during step 102 when the capsule is in the vicinity of the malignant cells that had been identified by previous tests, using known methods like PET, X-rays, NMR imaging or CT scans or a previous passage of another capsule. In some embodiments, this step 102 may include using electroporation or sonoporation to enhance the uptake of the fluorescent-labeled probe based on electric fields or ultrasonic waves or both emitted from the capsule or from external electrodes or transducers.

In some embodiments, once the cancer is confirmed and the capsule is positioned near the malignant cells during step 140, drug therapy is initiated by releasing one or more anticancer agents locally from one or more reservoirs on the capsule in step 170. The local release of drugs from the capsule permits the local or topical administration to cancer cells of concentrated, highly toxic drugs in relatively high doses with minimal side effects to the patient's normal cells. In some embodiments, this step may include using electroporation or sonoporation to enhance the uptake of the drug based on electric fields or ultrasonic waves or both emitted from the capsule or from external electrodes or transducers. This noninvasive method is not limited to the identification and treatment of cancer, but is applicable to treat any abnormal or diseased cells.

This method is not limited to chemical anticancer drugs but may include radioactive agents and photo-sensitizers. For example, in some embodiments, the capsule is used to deliver radioactive drugs locally. In some embodiments, the radiation is attached to compounds that are selectively targeted to abnormal cells. In this way, the radiation aimed selectively at the diseased cells such as cancer cells. While the radiation may penetrate normal cells in the vicinity of the cancer cells, the local release of the isotopes will minimize harm to normal cells throughout the body. In other embodiments, both anti-cancer drugs and radio-labeled drugs are released from the capsule for highly focused, localized combination drug therapy.

In some embodiments, this step may include the release of the photo-sensitizers and enhanced uptake using electroporation or sonoporation. In these embodiments, once the photosensitizers are released, they are activated by illumination from the light source. The local illumination of photo-sensitizers from the capsule permits the toxins to be used in relatively high doses with minimal side effects to the patient's normal cells. This noninvasive method is not limited to the identification and treatment of cancer, but is applicable to treat any abnormal or diseased cells.

The present system can also be used to evaluate the efficacy of treatment using the same camera that detects the uptake of the fluorescent probe. In one embodiment of step 170, the amount and distribution of fluorescence before and after treatment is determined by the same capsule. In such embodiments the position of a capsule in a body lumen is maintained during step 170 using a movement control system, such as one of the movement control systems described in more detail below. In other embodiments, a second capsule determines the measurements after treatment. In some embodiments a third capsule applies the treatment. An example of the embodiment of step 170 in which the amount and distribution of fluorescence before and after treatment is determined by the same capsule is described in the following paragraph.

The amount and distribution before treatment is determined as described above to obtain a baseline. Most anticancer agents are known to act very quickly once they are internalized. Therefore, for many cancer treatments the capsule is maintained in position for a relatively short interval of time ranging from about 20 to about 60 minutes following administration of the anticancer drugs. This time estimate is based on reports of increased binding of Annexin V and reduced uptake of phosphonium cations measured using PET within 20 to 60 min after administration of clinical doses of the anticancer drug taxol (Madar et al., JNM, vol. 44, p 179P, 2003) After this time, a second pulse of the same fluorescent-labeled probe is released from a reservoir on the capsule. The second pulse is controlled to be equivalent to the first administration of the probe. In embodiments in which endogenous fluorescence is used, this step can be omitted. The appropriate wavelength of excitation light is again emitted from the capsule to excite the fluorescence of the target molecule. The intensity and location of the fluorescent signal is collected and analyzed, and an image is optionally generated. Comparison of the amount of fluorescence before and after treatment is used to determine the efficacy of treatment. If a signal indicative of malignancy is decreased after treatment compared to baseline levels before therapy, it can be concluded that the number of cancer cells or their ability to take up the fluorescent molecule has decreased. A quantitative comparison yields a quantitative estimate of treatment efficacy.

4. System for Performing Functional Imaging 4.1 Structural Overview

Figure 2:
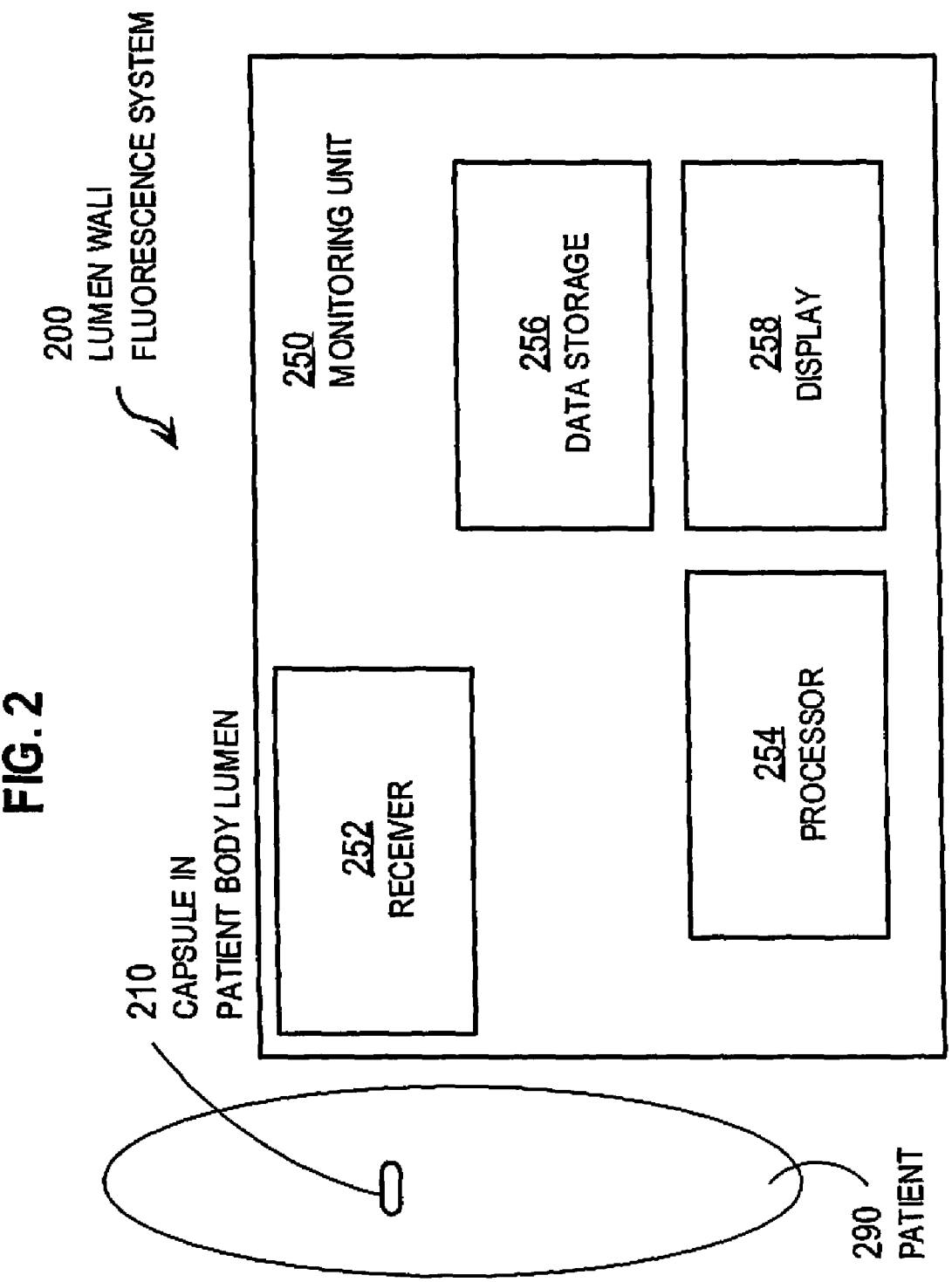
FIG. 2 is a block diagram that illustrates a system for detecting fluorescence in a body lumen wall, according to an embodiment.

FIG. 2 is a block diagram that illustrates a system 200 for detecting fluorescence in a body lumen wall of a patient 290 using a capsule 210, according to an embodiment. In the illustrated embodiment, capsule 210 resides in a body lumen of the patient 290. The system includes a monitoring unit 250 external to the patient 290. Patient 290 may be any animal including a human being.

The monitoring unit includes a receiver 252 for receiving rf transmissions from a data transfer system on the capsule 210, a processor 254 for processing fluorescence data received from the capsule and receiver to generate results, data storage 256 to store fluorescence data or results or both, and a display 258 to present fluorescence data or results or both to a user.

In the illustrated embodiment, the receiver 252 includes multiple rf antennae which receive rf transmissions carrying data from the detector on the capsule 210. The receiver 252 also generates data about the position of the capsule 210 within patient 290 based on the amplitudes of the received transmissions at the multiple antennae, as described above and in Iddan I.

The processor 254 generates an image from the position and fluorescence detector data, making corrections for the optics properties and geometry of the light source and fluorescence detector elements. In some embodiments, the computations and corrections are split between monitoring unit processor 254 and a processor on the capsule 210, if any.

The data storage 256 stores data from the processor or receiver or both, for example on a videotape recorder. The display presents the data or images from the processor or data storage, such as on printouts, color prints, or on a computer monitor, for a user such as a lab technician or medical doctor.

In other embodiments fewer components are included in monitoring unit 250. For example, some monitoring units do not include data display 258. The component of data storage 256 records data and results on one or more storage media. The data is then transferred from the data storage media to a display device in another location, such as by sending the media to the new location, or by sending data from the storage media over the internet, or by sending that data over a wireless communication device, or some combination.

4.2 Autonomous Capsule Assembly

Figure 3A:
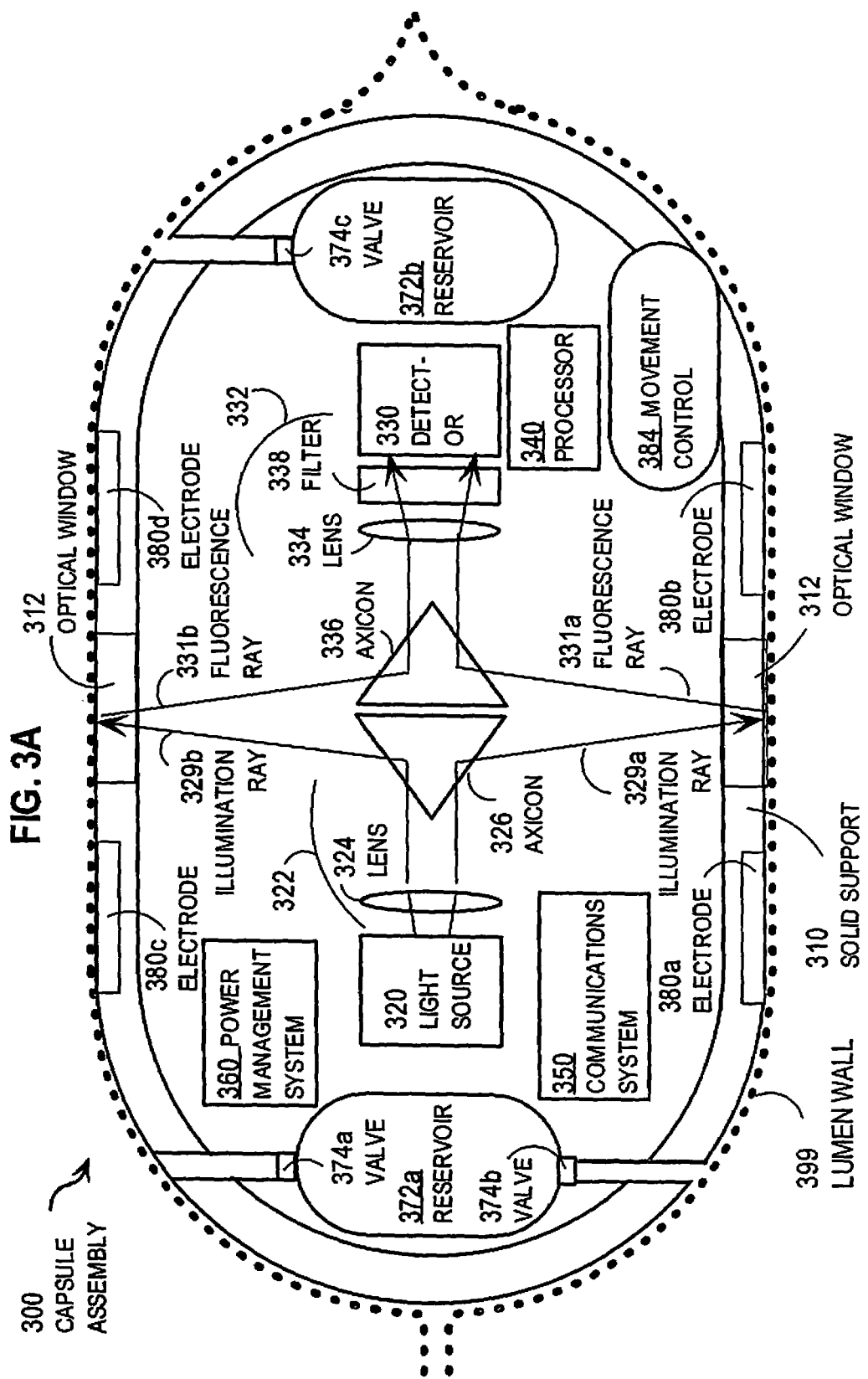
FIG. 3A is a block diagram that illustrates a swallowable capsule for detecting fluorescence in a body lumen wall, according to an embodiment.

FIG. 3A is a block diagram that illustrates a swallowable, indigestible capsule 300 for detecting fluorescence in a body lumen wall, according to an embodiment. The capsule is depicted in situ in a body lumen represented by lumen wall 399. The capsule includes a solid support 310, a light source 320, a source optical assembly 322, a detector 330, a detector optical assembly 332, a processor 340, a communications system 350, a power management system 360, reservoirs 372, electrodes 380, and movement control system 384.

The solid support 310 is shown as a surrounding body of a suitable material. For example a capsule swallowed by a patient is made of a material, such as a plastic material, that is not digested while in the caustic environment of the stomach. In some embodiments some or the entire outer surface of the capsule is flexible. In some embodiments the solid support is, or includes, a chassis internal to the capsule, to which separate components or subsystems are attached. Any materials known in the art that are suitable for the lumen environment may be used.

Attached to the solid support 310 is a light source 320 to excite the fluorescent signal of the target molecule, such as an endogenous molecule like collagen or an exogenous molecule like a fluorescent PhC probe molecule bound in the intestinal wall. A variety of light-emitting diodes (LEDs) that emit light at a variety of different wavelengths with a variety of different wavelength bands are well known in the art. In some embodiments a LED is selected to match the excitation wavelength of the target molecule. In some embodiments, the light source has a broad spectrum, such as a white light LED. In other embodiments, other light sources are used. If a narrow spectrum light source is not available with a particular excitation wavelength, a light source with a broad spectrum is used that includes the excitation wavelength. In some embodiments, the light source is pulsed to save energy or to provide temporal separation of excitation and fluorescent light or both.

For purposes of illustration, it is assumed that, in an example embodiment, the excitation wavelength for the fluorescent marker bound to a PhC probe is $\lambda 0$ and the fluorescent signal emitted by this particular fluorescent marker includes wavelength $\lambda F$. In this case the light source 320 emits light at $\lambda 0$ with a substantial intensity.

In some embodiments, especially when selected probe molecules are used to label tumor cells, illumination at selective wavelengths activates photo-active toxins which are used in therapeutic applications of the capsule. For example a bright white LED can be used to activate any of multiple photo-active toxins.

The source optical assembly 322 includes a combination of one or more optical elements to direct light of the excitation wavelength to the lumen wall 399. Any method to shine the excitation wavelength $\lambda 0$ onto the lumen wall 399 may be used. In the illustrated embodiment, the source optical assembly 322 includes an optical window 312 transparent to the excitation wavelength $\lambda 0$ and the fluorescent wavelength $\lambda F$ in solid support 310, an axicon 326, and a lens 324. In other embodiments, more or different optical elements are included, such as a transparent dome and other elements that allow fluorescence excitation and detection by light more closely parallel to a longitudinal axis of the probe.

In the illustrated embodiment, the optical window 312 is a band that encircles the capsule at a particular axial position. FIG. 3B is a perspective drawing to indicate three dimensional directions and coordinates relative to the capsule, according to an embodiment. In FIG. 3B, the capsule assembly 300 has an axial direction 314 along the longitudinal axis of the capsule that is often parallel to the local direction of the body lumen and the local direction of movement of the capsule through the body lumen. One position 315 on the capsule along the longitudinal axis is taken as the origin of a relative, internal coordinate system for the capsule. In a plane perpendicular to the axial direction 314 at the origin 315 are multiple line segments that radiate from the origin 315 to indicated a first transverse direction 316*a* and a second transverse direction 316*b*. The first transverse direction 316*a* is the radial axis for the capsule. The two are separated by an azimuthal angle 317 from the radial axis 316*a* to the second transverse direction 316*b* in the perpendicular plane. For a polar coordinate system, a ray from the origin 315 along the axial direction is called the z axis, the ray from the origin 315 along radial axis 316*a* called the 0 azimuth axis ("x axis") and the second dimension is the azimuthal angle from the x axis, and the third dimension is distance from the origin along the transverse direction to a point. For a Cartesian coordinate system, the third dimension is a ray from the origin 315 perpendicular to both the x axis and the z axis which is called the y axis and the coordinates of a point are the distances on the x, y, and z axes.

In the illustrated embodiment, the optical window 312 is a circular band. A circle formed by the points in the middle of the optical window is the mid-window circumference 313. The origin 315 is selected at the particular axial position that forms the center of the mid-window circumference 313. The optical window 312 exposes a cylindrical section of the body lumen to light at the excitation wavelength $\lambda 0$. The section can be illuminated simultaneously or different portions of the section can be illuminated at different times. For complete coverage of the body lumen, the entire section should be illuminated before the capsule travels a distance along the lumen equal to the width of the optical window in the axial direction 314.

In some embodiments, the optical window forms a continuous band around the capsule as indicated in FIG. 3B; in other embodiments, the band is constituted from a series of sections transparent to the excitation wavelength separated by one or more sections opaque to the excitation wavelength where structural members cross the window. For example, an opaque section may carry one or more conductors to connect a power supply on one side of the capsule to components that use power on the other side of the capsule, or connect data collected on one side of the capsule with a processor 340 or communications system 350 on an opposite side of the capsule, or some combination of these or other connections.

In other embodiments, the optical window is shaped differently. For example, in some embodiments the optical window is a dome at either axial end of the capsule. The dome is made of material that is transparent to the excitation and fluorescent wavelengths $\lambda 0$ and $\lambda F$. In any embodiment, the source optical assembly 322 is configured to emit the excitation wavelength light through the optical window.

In the illustrated embodiment in FIG. 3A, the source optical assembly includes a lens 324 that focuses a parallel beam of light from the light source onto an axis of rotation of an axicon 326. An axicon is a conical section of transparent or reflective material. In some embodiments, its shape is formed by rotating a triangle or trapezoid around an axis of rotation. In other embodiments, the hypotenuse of the triangle is replaced by a curved line connecting the vertices, thus allowing some focusing of the light. An axicon converts a beam of light that is incident on its axis of rotation into a circular band or ring of light. An axicon also converts a band of light incident on its conical surface to a beam of light parallel to its axis of rotation. Axicons are well known in the art. For example, the propagation of light through an axicon and design of axicons are described by L. L. Doskolovich, S. N. Khonina, V. V. Kotlyar, I. V. Nikolsky, V. A. Soifer, and G. V. Uspleniev in "Focusators into a ring," Optical and Quantum Electronics v 25, pp. 801-814, 1993, and A. Thaning, A. T. Friberg and Z. Jaroszewicz in "Synthesis of diffractive axicons for partially coherent light based on asymptotic wave theory," Optics Letters, v 26, No. 21, pp. 1648-1650, November 2001, the entire contents of each of which are hereby incorporated by reference as if fully set forth herein.

The lens 324 and axicon form a ring of light that propagates through the circular band optical window 312 and illuminates the lumen wall 399. By forming a ring of light that matches the dimensions of optical window 312, energy wasted in generating light that does not excite fluorescence is greatly reduced and precious power on board the capsule is preserved. To match the optical window 312, the axicon 326 is positioned near the origin at the center of the mid-window circumference, and its axis of rotation is aligned with the axial direction 314.

In other embodiments, the source optical assembly 322 includes different components to direct excitation light through optical window 312. For example, in some embodiments, in the source optical assembly 322 axicon 326 is replaced with a rotating mirror angled to deflect a light beam from light source 320 though window 312 in a sweep through azimuthal angles from 0 to 360 degrees over one or more pulses from light source 320. The lens 324 is replaced by one or more different lenses that focus a beam on the rotating mirror.

In yet another embodiment, in the source optical assembly 322 the axicon 326 is replaced with a bundle of optical fibers, each of which provides a waveguide for light of the excitation wavelength $\lambda 0$ from the source 320 to the optical window 312 at a different azimuthal angle. In some embodiments lens 324 is omitted or replaced with one or more lenses to couple light into the bundle of optical fibers.

In some embodiments, the source optical assembly 322 includes a filter, not shown, which filters out the fluorescent wavelength $\lambda F$ from the light emitted by the source 320. In some embodiments, the source optical assembly 322 includes one or more filters, not shown, which filter out most wavelengths other than the excitation wavelength $\lambda 0$ from the light emitted by the source 320.

Attached to the solid support is a detector 330 to sense the fluorescent signal of the target molecule, such as wavelength $\lambda F$ from the fluorescent marker on the PhC probe molecule. In some embodiments, a single sensor is used to detect all light at wavelength $\lambda F$ from any portion of the lumen wall. In other embodiments an array of sensors is used to separately detect light at wavelength $\lambda F$ from different portions of the illuminated section of the lumen wall. The different portions may represent different portions of the lumen wall in the axial direction or the azimuthal direction or both, depending on an optical assembly that carries the fluorescent light and an arrangement of the array of sensors. Any light sensor may be used, such as a charge-coupled device (CCD) and a complimentary metal oxide semiconductor (CMOS). In the example embodiment, an array of CCDs is used. In some embodiments, three CCD arrays are used to distinguish three colors as is commercially available as components for miniature color video cameras. In some embodiments, a single CCD array is used. In the illustrated embodiment, the data generated by each sensor in detector 330 not only indicates detection of a threshold number of photons, but also indicates the intensity, i.e., a value that is proportional to the number of photons incident on the detector during a sensor integration time.

The detector optical assembly 332 includes a combination of one or more optical elements to direct light of the fluorescent wavelength from the lumen wall 399 to the detector 330. Any method to direct the fluorescent wavelength $\lambda F$ onto the detector 330 may be used. In the illustrated embodiment, the detector optical assembly 332 includes the optical window 312 in solid support 310, an axicon 336, a lens 334, and a filter 338. In other embodiments, more or different optical elements are included.

In the illustrated embodiment, the optical window 312 is a circular band. In other embodiments, the optical window is shaped differently. In any embodiment, the detector optical assembly 332 is configured to direct the fluorescent wavelength light transmitted through the optical window 312 from lumen wall 399 to the detector 330.

In the illustrated embodiment, the detector optical assembly 332 includes axicon 336 to convert a circular band of light incident on its conical surface to a beam of light parallel to its axis of rotation. In some embodiments, using a single sensor in detector 330, the optical properties of axicon 336 and lens 334 are selected to match axicon 326 so that the fluorescent light received from the circular band optical window 312 forms a single beam incident on the detector. In embodiments with an array of sensors in detector 330, the optical properties of axicon 336 and lens 334 are selected to differ from axicon 326 so that the fluorescent light received from different portions of the circular band optical window 312 are focused on different sensors of the detector 330. By focusing on the detector 330 a ring of light that matches the dimensions of optical window 312, fluorescent energy emitted from the illuminated section of the lumen wall is not wasted by failing to fall on the detector, and the efficiency of the capsule is improved. To match the optical window 312, the axicon 336 is positioned near the origin at the center of the mid-window circumference, and its axis of rotation is aligned with the axial direction 314.

In other embodiments, the detector optical assembly 332 includes different components to direct fluorescent light from optical window 312 onto the detector. For example, in some embodiments in the detector optical assembly 332 the axicon 336 is replaced with a rotating mirror angled to deflect a light beam from window 312 in a sweep through azimuthal angles from 0 to 360 degrees. The resulting beam can be measured with a single sensor that uses time differences to differentiate the fluorescence originating at different azimuths. In such embodiments, the mirror in detector optical assembly 332 is offset from a rotating mirror in the source optical assembly 322 to reflect a portion of the lumen wall that is not currently illuminated but instead reflects a portion of the lumen wall is just after illumination. In some embodiments a spatial array at detector 330 is used to distinguish different axial positions at each azimuth.

In yet another embodiment, in the detector optical assembly 332 the axicon 336 is replaced with a bundle of optical fibers, each of which provides a waveguide for light of the fluorescent wavelength $\lambda F$ from the optical window 312 at a different azimuthal angle to a different sensor on the detector 330. In some embodiments lens 334 is omitted or replaced with one or more lenses to couple light from the bundle of optical fibers.

The detector optical assembly 332 includes a filter 338 which filters out the excitation wavelength λ0 from the light received from optical window 312. In some embodiments, the detector optical assembly 332 includes one or more filters 338 which filter out most wavelengths other than the fluorescent wavelength λF from the light received from the optical window 312. In some embodiments, filter 338 is omitted. For example, filter 338 is omitted in some embodiments that use a filter in the source optical assembly 322.

In some embodiments, the detector optical assembly 332 includes multiple filters 338, each of which filters out most wavelengths other than one of several fluorescent wavelengths of interest from the light received from optical window 312 and directed onto an array of one or more sensors in detector 330. The several wavelengths of interest may be from the same fluorescent marker or from different markers used in different methods that employ the capsule. For example, it is assumed for purposes of illustration that the fluorescent marker bound to PhC fluoresces at three wavelengths λF1, λF2, λF3. The 3-color detector used in color video cameras can be used with three filters for these three wavelengths instead of the standard red, green and blue filters. The resulting data can be processed to eliminate spurious sources of any one of these wavelengths and increase the accuracy and reliability of the measurements of fluorescence. In another example, the three filters pass three wavelengths in the endogenous fluorescence spectrum of collagen, e.g., at red-brown, yellow, and green. The red shift of collagen in abnormal cells is then determined by computing ratios of the intensity received at the detector behind the red-brown filter to the intensities received at the detectors behind the yellow and green filters.

In some embodiments, the multiple filters are used for multiple different fluorophores. For example, if both PhCs and collagen are used as fluorophores to more accurately determine malignant cells, the capsule can use one filter and detector array for the PhC fluorescent label and two filters and corresponding detector arrays for red-brown and yellow-green to determine the red shift in collagen. As another example, the multiple filters are used to distinguish multiple endogenous fluorophores such as tryptophan, tyrosine, NADH, riboflavin.

In another example, the three different wavelengths are used for three different fluorophores used in entirely different protocols for unrelated pathologies. The same model capsule can be used to detect any of the three fluorophores by processing data only from the detector array filtered for the appropriate wavelength. Three different capsules do not have to be manufactured. In some embodiments a single detector array is used, and the filters 338 are moveably mounted to solid support 310 so that a different filter can be positioned in front of the single array under control of a user of the capsule.

In some embodiments the detector optical assembly 332 includes a shutter, not shown, that is closed when the light source is on and is open when the light source 320 is off. In some embodiments, the shutter is operated so that fluorescence can be detected in a time interval after illumination when the detector is not contaminated by light from the source.

Processor 340 is an information processor. For example, in some embodiments processor 340 is a microprocessor specifically designed for the capsule 300, such as an application specific integrated circuit (ASIC). In some embodiments, processor 340 is a general-purpose signal processing or computer chip programmed by software to function in a particular way, as described in more detail in a later section. Processor is configured to control the operation of the other components in the capsule 300, such as light source 320, and to collect data based on measurements from detector 330.

For example, in some embodiments processor 340 determines pixels representing fluorescent intensity at each portion of the illuminated section and associates a 3-D coordinate (such as distance along the z axis, distance from the origin in a transverse direction, and azimuth angle from the transverse direction to the x axis, or x, y, z coordinates). In some embodiments that use a single measurement from all azimuths, the processor 340 need not compute a coordinate to go with the integrated intensity.

In some embodiments, processor 340 is also configured to perform some of the diagnosis and therapy decisions described above based on the measurements made by detector 330 or data communicated from the monitoring unit 250 or both. For example, processor 340 determines the ratio of intensities at detectors behind red-brown and yellow-green filters and determines when the ratio crosses a threshold that indicates a malignant lesion based on endogenous fluorescence from collagen.

The communications system 350 sends data based on measurements from the sensor to the monitoring unit 250. In some embodiments, communications system 350 also receives data that indicates commands or instructions to the capsule. For example, the communications system 350 receives data that indicates which filter 338 should be disposed in front of the detector 330. Any communication system that can safely send data through a patient can be used. For example a rf communication system, such as described in Iddan I, is used in some embodiments. In some embodiments an acoustic system is used.

A power management system 360 is included in capsule 300. Any appropriate power supply or power supply and management system known in the art can be used as power management system 360. Elements of power management systems are described in several patents, including U.S. Pat. No. 6,428,469 by G. V. Iddan and G. Meron issued Aug. 6, 2002 (hereinafter Iddan II), the entire contents of which are hereby incorporated by reference as if fully set forth herein. In particular, the NORIKA capsule is at least partly powered by a wireless power transfer system that uses currents induced in the capsule by an external fluctuating magnetic field. Elements of a wireless power transfer systems are described in several patents and publications, including U.S. Pat. No. 5,170,801 by R. A. Casper, M. J. McCartney, W. J. Jochem and A. F. Parr issued Dec. 15, 1992 (hereinafter Casper) and U.S. Patent Application Pub. No. US2002/0165592 by A. Glukhovsky, G. J. Iddan and G. Meron published Nov. 7, 2002 (hereinafter Glukhovsky) the entire contents of each of which are hereby incorporated by reference as if fully set forth herein.

Reservoirs 372, including reservoirs 372a, 372b are included in the illustrated embodiment. In other embodiments, more or fewer or no reservoirs are included. In other embodiments the positions of reservoirs 272 are modified, for example to accommodate a dome optical window at one or both ends of the capsule for fluorescence measurements along the axial direction. In the illustrated embodiment reservoir 372a holds a supply of a fluorescent-labeled probe that is photo-toxic when activated using selected wavelengths and intensities; and reservoir 372b holds a supply of a medicine to dispense to kill abnormal cells detected based on the fluorescence measurements by detector 330. Each reservoir has a release mechanism for releasing its contents to the body lumen on command. For example, reservoir 372a includes valves 374a, 374b and reservoir 372b includes valve 374c. In other embodiments, reservoirs 372 include more or fewer release mechanisms.

In some embodiments, reservoirs 372 are placed to operate as the capsule 300 moves through the body lumen. For example, reservoir 372a releases some of its contents at a leading edge of the capsules movement through the lumen so that the contents are taken up by the cells in the lumen wall by the time the optical window 312 passes over that section. Then the probes are in place in the cell wall for excitation by the illumination from source 320 through window 312. Fluorescence is measured based on the probes taken up by the cells and it is determined whether cancer is present locally. If it is determined that cancer cells are present locally then local therapy is applied, depending on the embodiment. For example, if a photo-active toxin has been administered, then the light source is illuminated again to activate the photo-active toxin and kill the cells that concentrated the photo-active toxin. If a topically applied drug stored in reservoir 374b is to be administered, then valve 374c is opened to dispense the drug in the vicinity of the abnormal cells. The release can be timed so that openings, through which the valves 374c pass the contents of a reservoir 372b, are in the position determined to have the abnormal cells.

In the illustrated embodiment, the capsule includes electrodes 380, including electrodes 380a, 380b, 380c, 380d. Electrodes 380 are operated to enhance uptake by the cells in the lumen wall of the contents released from reservoirs 372. In some embodiments the probes or drug contained in the reservoirs, or both, are charged, e.g., positively charged. An electric field is applied using electrodes 380 to move charged probes in a particular direction via electromigration to produce transport into the tissue. If the electric field is formed in repeated short pulses of microsecond to millisecond duration, some cell membranes become permeable, thus allowing penetration of the probe or drug into the cell by the process termed electroporation. Electroporation is well known in the art and has been shown to increase uptake of lysomes by a factor of about five. In one embodiment, electrode 380a is a band that includes electrode 280c and is charged at one voltage relative to a second band that includes electrode 380b and 380d.

In some embodiments, the capsule includes an acoustic transducer (not shown) in addition to or instead of one or more electrodes 380. In some such embodiments the acoustic transducer is operated at ultrasound frequencies to enhance uptake of the probes or drugs, or both, through sonoporation a process which has been well established.

In the illustrated embodiment, capsule 300 includes components of a movement control system 384. A movement control system includes one or more components on capsule 300 for reducing, negating or overriding the peristaltic action of the intestine. In some embodiments the capsule is able to maintain a fixed position or move against the direction of the peristaltic action or orient itself in a particular direction. Elements of such movement control systems are described in several publications, including U.S. Patent Application Pub. No. US2003/0092964 by B. Kim, Y. Jeong, T. Kim, J. Park and S. Song published May 15, 2003, and U.S. Patent Application Pub. No. US2003/0092964 by B. Kim, Y. Jeong, T. Kim, J. Park and S. Song published May 15, 2003, the entire contents of each of which are hereby incorporated by reference as if fully set forth herein. These embodiments use extensible fins or pellets to move the capsule relative to the lumen wall. These systems may also be used to orient a small capsule in the large intestine to offset forces that might otherwise cause the capsule to tumble while passing through the large intestine.

A magnetic stator and rotor system is described at the time of this writing on world wide web pages of the internet at domain name rfnorika.com, cited above, to change orientation of a capsule inside a patient's intestine. Three coils are placed at intervals inside the capsule to play the role of rotor coils. Three coils embedded in a vest worn by the patient act as stators and set up magnetic fields to determine a direction of rotation. A capacitor on the capsule is charged. When the capacitor is discharged through the rotor coils a large transient magnetic force is generated by the capsule which interacts with the external magnetic field set up by the stators to cause the capsule to rotate. The capsule tilt is determined within 15 degrees by monitoring the current flowing through the rotor coils and the stator coils. In embodiments using this system, the capsule movement control system 384 includes the capacitor and the rotor coils.

In some embodiments, the movement control system is used so that a single capsule can remain in place to monitor the efficacy of treatment of a disease with fluorescent indicators, as described above. In some embodiments, the movement control system is used so that a single capsule can remain in place to detect and then treat abnormal cells.

In some embodiments, capsule 300 includes a sample collection system (not shown) to sample tissue from the lumen wall at the current position of the capsule based on the fluorescent measurements from detector 330. Any appropriate method known in the art to sample tissue from a capsule passed through the body lumen may be used. In one embodiment, a suction pump is added to the capsule and a biopsy is taken by aspiration. In another embodiment, the elliptic head of the capsule is used as a spoon for mechanical collection of a tissue sample, using a movement control system, such as the magnetic field rotor-stator to twist the spoon.

4.3 External Assembly

In some embodiments the external assembly includes more or different components than are depicted in monitoring unit 250. For example, in some embodiments monitoring unit 250 includes a separate positioning system to determine the position of the capsule in the patient, a movement control system to control movement of the capsule through the patient, a rf transmitter to transmit data and commands to the capsule, and a power management system.

A positioning system is used to detect the location of the capsule as it moves through the intestines (such as by peristaltic action by muscles on the intestine). An example position system is described in Iddan I, cited above. The location is detected based on the power of the rf transmission received at each of an array of antennae placed outside the patient. Receiver 252 in the illustrated embodiment includes such an array of antennae. In some embodiments an acoustic tracking system is used in which the capsule emits acoustic waves that are detected by acoustic sensors distributed around the patient. In other embodiments a magnetic tracking system based on the magnetic Barkhausen effect is used. Such a system is described in U.S. Pat. No. 6,337,627 by R. J. Von Gutfeld, J. F. Ziegler, S. J. McAllister, J. H. Anderson, J. C. Murphy and M. D. Ziegler, issued Jan. 8, 2002 (hereinafter Von Gutfeld) the entire contents of which are hereby incorporated by reference as if fully set forth herein.

Processor 254 is an information processor. For example, in some embodiments processor 254 is a microprocessor specifically designed for the monitoring system 250, such as an application specific integrated circuit (ASIC). In some embodiments, processor 254 is a general-purpose signal processing or computer chip programmed by software to function in a particular way, as described in more detail in a later section. Processor 254 is configured to control the operation of the other components in the monitoring system 250 and the capsule 300 and to receive input from a user.

For example, in some embodiments processor 254 determines pixels representing fluorescent intensity at each portion of the illuminated section and associates a 1-D, 2-D or 3-D coordinate with the pixel. In some embodiments, the processor generates an image based on the pixel data and stores the image on data storage 256 and displays the image on data display 258. In some embodiments processor 254 determines the ratio of intensity at difference fluorescent wavelengths.

In some embodiments, processor 254 is also configured to perform some of the diagnosis and therapy decisions described above based on the measurements made by capsule 300, measurements by receiver 252, or information communicated from a user, or some combination of these information sources.

In some embodiments, monitoring unit 250 includes components of a power management system (not shown). For example, monitoring unit includes coils for a fluctuating magnetic field used to induce currents in coils on the capsule 300 to transmit power to capsule 300 without wires, as described above and in Iddan II, Casper, and Glukhovsky.

In some embodiment, monitoring unit 250 includes components of a movement control system (not shown) described above. For example, monitoring unit 250 includes the three coils embedded in a vest worn by the patient, which act as stators and which set up magnetic fields to determine a direction of rotation for the capsule 300. The movement control system in monitoring unit 250 also determines the capsule tilt within 15 degrees by monitoring the current flowing through the rotor coils on the capsule and the stator coils in the vest. The position control system is operated in some embodiments to position the capsule to take a biopsy, and in some embodiments to release material from a particular reservoir with an opening on only one side of the capsule.

5. Processor Hardware Overview

Figure 4:
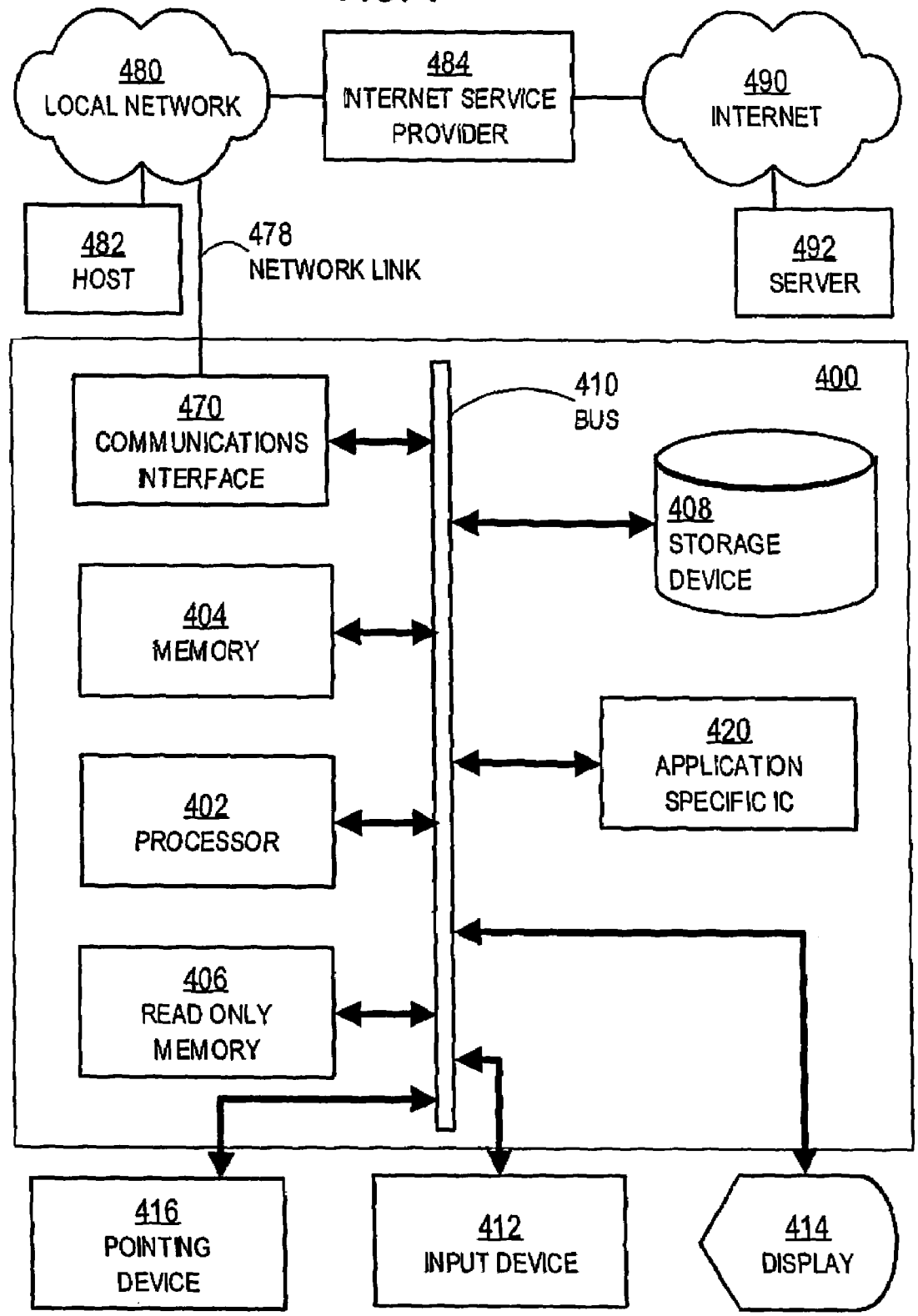
FIG. 4 is a block diagram that illustrates a computer system upon which a portion of an embodiment of the invention may be implemented.

FIG. 4 is a block diagram that illustrates a computer system 400 upon which portions of an embodiment of the invention may be implemented. For example, in some embodiments, functions performed by the processor of the monitoring unit may be performed by computer system 400. Computer system 400 includes a communication mechanism such as a bus 410 for passing information between other internal and external components of the computer system 400. Information is represented as physical signals of a measurable phenomenon, typically electric voltages, but including, in other embodiments, such phenomena as magnetic, electromagnetic, pressure, chemical, molecular and atomic interactions. For example, north and south magnetic fields, or a zero and non-zero electric voltage, represent two states (0, 1) of a binary digit (bit). A sequence of binary digits constitutes digital data that is used to represent a number or code for a character. A bus 410 includes many parallel conductors of information so that information is transferred quickly among devices coupled to the bus 410. One or more processors 402 for processing information are coupled with the bus 410. A processor 402 performs a set of operations on information. The set of operations include bringing information in from the bus 410 and placing information on the bus 410. The set of operations also typically include comparing two or more units of information, shifting positions of units of information, and combining two or more units of information, such as by addition or multiplication. A sequence of operations to be executed by the processor 402 constitute computer instructions.

Computer system 400 also includes a memory 404 coupled to bus 410. The memory 404, such as a random access memory (RAM) or other dynamic storage device, stores information including computer instructions. Dynamic memory allows information stored therein to be changed by the computer system 400. RAM allows a unit of information stored at a location called a memory address to be stored and retrieved independently of information at neighboring addresses. The memory 404 is also used by the processor 402 to store temporary values during execution of computer instructions. The computer system 400 also includes a read only memory (ROM) 406 or other static storage device coupled to the bus 410 for storing static information, including instructions, that is not changed by the computer system 400. Also coupled to bus 410 is a non-volatile (persistent) storage device 408, such as a magnetic disk or optical disk, for storing information, including instructions, that persists even when the computer system 400 is turned off or otherwise loses power.

Information, including instructions, is provided to the bus 410 for use by the processor from an external input device 412, such as a keyboard containing alphanumeric keys operated by a human user, or a sensor. A sensor detects conditions in its vicinity and transforms those detections into signals compatible with the signals used to represent information in computer system 400. Other external devices coupled to bus 410, used primarily for interacting with humans, include a display device 414, such as a cathode ray tube (CRT) or a liquid crystal display (LCD), for presenting images, and a pointing device 416, such as a mouse or a trackball or cursor direction keys, for controlling a position of a small cursor image presented on the display 414 and issuing commands associated with graphical elements presented on the display 414.

In the illustrated embodiment, special purpose hardware, such as an application specific integrated circuit (IC) 420, is coupled to bus 410. The special purpose hardware is configured to perform operations not performed by processor 402 quickly enough for special purposes. Examples of application specific ICs include graphics accelerator cards for generating images for display 414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 400 also includes one or more instances of a communications interface 470 coupled to bus 410. Communication interface 470 provides a two-way communication coupling to a variety of external devices that operate with their own processors, such as printers, scanners and external disks. In general the coupling is with a network link 478 that is connected to a local network 480 to which a variety of external devices with their own processors are connected. For example, communication interface 470 may be a parallel port or a serial port or a universal serial bus (USB) port on a personal computer. In some embodiments, communications interface 470 is an integrated services digital network (ISDN) card or a digital subscriber line (DSL) card or a telephone modem that provides an information communication connection to a corresponding type of telephone line. In some embodiments, a communication interface 470 is a cable modem that converts signals on bus 410 into signals for a communication connection over a coaxial cable or into optical signals for a communication connection over a fiber optic cable. As another example, communications interface 470 may be a local area network (LAN) card to provide a data communication connection to a compatible LAN, such as Ethernet. Wireless links may also be implemented. For wireless links, the communications interface 470 sends and receives electrical, acoustic or electromagnetic signals, including infrared and optical signals, that carry information streams, such as digital data. Such signals are examples of carrier waves.

The term computer-readable medium is used herein to refer to any medium that participates in providing instructions to processor 402 for execution. Such a medium may take many forms, including, but not limited to, non-volatile media, volatile media and transmission media. Non-volatile media include, for example, optical or magnetic disks, such as storage device 408. Volatile media include, for example, dynamic memory 404. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 478 typically provides information communication through one or more networks to other devices that use or process the information. For example, network link 478 may provide a connection through local network 480 to a host computer 482 or to equipment 484 operated by an Internet Service Provider (ISP). ISP equipment 484 in turn provides data communication services through the public, world-wide packet-switching communication network of networks now commonly referred to as the Internet 490. A computer called a server 492 connected to the Internet provides a service in response to information received over the Internet. For example, server 492 provides information representing video data for presentation at display 414.

The invention is related to the use of computer system 400 for implementing the techniques described herein. According to one embodiment of the invention, those techniques are performed by computer system 400 in response to processor 402 executing one or more sequences of one or more instructions contained in memory 404. Such instructions, also called software and program code, may be read into memory 404 from another computer-readable medium such as storage device 408. Execution of the sequences of instructions contained in memory 404 causes processor 402 to Perform the method steps described herein. In alternative embodiments, hardware, such as application specific integrated circuit 420, may be used in place of or in combination with software to implement the invention. Thus, embodiments of the invention are not limited to any specific combination of hardware and software.

The signals transmitted over network link 478 and other networks through communications interface 470, which carry information to and from computer system 400, are exemplary forms of carrier waves. Computer system 400 can send and receive information, including program code, through the networks 480, 490 among others, through network link 478 and communications interface 470. In an example using the Internet 490, a server 492 transmits program code for a particular application, requested by a message sent from computer 400, through Internet 490, ISP equipment 484, local network 480 and communications interface 470. The received code may be executed by processor 402 as it is received, or may be stored in storage device 408 or other non-volatile storage for later execution, or both. In this manner, computer system 400 may obtain application program code in the form of a carrier wave.

Various forms of computer readable media may be involved in carrying one or more sequence of instructions or data or both to processor 402 for execution. For example, instructions and data may initially be carried on a magnetic disk of a remote computer such as host 482. The remote computer loads the instructions and data into its dynamic memory and sends the instructions and data over a telephone line using a modem. A modem local to the computer system 400 receives the instructions and data on a telephone line and uses an infra-red transmitter to convert the instructions and data to an infra-red signal, a carrier wave serving as the network link 478. An infrared detector serving as communications interface 470 receives the instructions and data carried in the infrared signal and places information representing the instructions and data onto bus 410. Bus 410 carries the information to memory 404 from which processor 402 retrieves and executes the instructions using some of the data sent with the instructions. The instructions and data received in memory 404 may optionally be stored on storage device 408, either before or after execution by the processor 402.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for determining the efficacy of treatment of cancer in the upper and lower intestinal tract in an animal comprising the steps of:
   a. administering to the animal having cancer of the upper or lower intestinal tract an amount of an exogenous fluorescent-labeled probe that is selectively internalized or bound by the cancer cells;
   b. illuminating cells in the an intestinal wall of said animal from a light source mounted to a first autonomous solid support introduced into the lumen of the intestine with a wavelength that excites a particular fluorescent signal emitted by the fluorescent label on the exogenous probe in the cancer cells;
   c. detecting at a detector mounted to the first autonomous solid support the fluorescent signal emitted by the exogenous probe in cancer cells illuminated during step b to determine a first amount of fluorescent emission;
   d. after step c, administering treatment to the animal having cancer of the upper or lower intestinal tract to eliminate the cancer cells;
   e. after step d, administering to the animal an amount of the exogenous fluorescent-labeled probe;
   f. after step e, illuminating cells in the intestinal wall from a light source mounted to a second autonomous solid support introduced into the lumen of the intestine with the wavelength that excites the particular fluorescent signal;

g. detecting at a detector mounted to the second solid support the fluorescent signal emitted by the exogenous probe in cancer cells illuminated during step f to determine a second amount of fluorescent emission; and h. determining an efficacy of the treatment based on a difference between the first and second amounts of fluorescent emission.

2. The method as recited in claim 1, wherein the first autonomous solid support is the same as the second autonomous solid support.

3. The method as recited in claim 1, wherein the first autonomous solid support is different from the second autonomous solid support.

* * * * *